US United States Patent [19]

Walker

[11] 4,390,360
[45] Jun. 28, 1983

[54] CONTROL OF SICKLEPOD, SHOWY CROTALARIA, AND COFFEE SENNA WITH A FUNGAL PATHOGEN

[75] Inventor: Harrell L. Walker, Stoneville, Miss.

[73] Assignee: The United States of America as represented by the Secretary of Agriculture, Washington, D.C.

[21] Appl. No.: 356,870

[22] Filed: Mar. 10, 1982

[51] Int. Cl.³ .......................................... A01N 63/04
[52] U.S. Cl. .......................................... 71/79
[58] Field of Search .............................. 71/79

[56] References Cited

U.S. PATENT DOCUMENTS

| | | | |
|---|---|---|---|
| 3,849,104 | 11/1974 | Daniel et al. | 71/79 |
| 3,999,973 | 12/1976 | Templeton | 71/79 |
| 4,162,912 | 7/1979 | Charudattan | 71/79 |
| 4,263,036 | 4/1981 | Charudattan | 71/79 |

FOREIGN PATENT DOCUMENTS 343671   7/1972   U.S.S.R. .................................. 71/79

OTHER PUBLICATIONS

Husain et al., "Production of a Toxin, etc.", (1966), Labdeu J. Sci. Tech. 4 (2) pp. 144–146 (1966).
Fulton et al., "A Metabolite from A. Tenius, etc.," (1965), Phytopathology 55 pp. 49–51 (1955).

Primary Examiner—Glennon H. Hollrah
Attorney, Agent, or Firm—M. Howard Silverstein; David G. McConnell; Raymond C. Von Bodungen

[57] ABSTRACT

This invention relates to a method for biological control of multiple plant weeds, sicklepod, showy crotalaria, and coffee senna. The control is accomplished using a specific host strain of the fungus *Alternaria cassiae* to produce typical lesions in and kill the multiple weeds. *Alternaria cassiae* is on deposit with the USDA-SEA-AR Southern Weed Science Laboratory in Stoneville, Mississippi; the Mycological Services, Botany Department, University of Massachusetts, Amherst; and with the Agricultural Research Culture Collection (NRRC), Peoria, Illinois and assigned the #12553.

4 Claims, No Drawings

CONTROL OF SICKLEPOD, SHOWY CROTALARIA, AND COFFEE SENNA WITH A FUNGAL PATHOGEN

BACKGROUND OF THE INVENTION (1) Field of the Invention

The instant invention is a method for the control of undesirable plants by use of plant pathogens.

(2) Description of the Prior Art

The merits for using plant pathogens to control weeds in annual crops have been discussed previously for two Colletotrichum spp. (Daniel, et al. U.S. Pat. No. 3,999,973). The anthracnose fungus *Colletotrichum gloeosporioides* has been used to control the weed northern jointvetch, and another strain of this fungus has been used to control winged waterprimrose. *Colletotrichum malvarum* has been used to control prickly sida. These three pathogens have been combined to control all three target weeds at once. In other experimental work the fungus *Alternaria macrospora* has been used to control spurred anoda, *Alternaria macrospora*, Weed Science, L. Walker, 1981, Vol 29, pp 505–507.

A major constraint to commercial development of a plant pathogen as biological herbicide is selectivity. A pathogen that controls only one weed species in one crop does not have the same market potential as a pathogen that controls several important weeds in several crops.

Sicklepod (*Cassia obtusifolia L.*) is a major weed problem in much of the southern United States where soybeans and peanuts are grown. This non-nodulating legume is very competitive with these crop plants and can significantly reduce yields at low weed densities. Mature sicklepod plants commonly reach a height of 2 to 2.5 m. The weed produces large quantities of seeds that can germinate and grow under a wide range of environmental conditions. Seedlings characteristically have rounded cotyledons, 15–20 mm across, with 3 to 5 distinct veins in the upper leaf surface. The first leaves have 3–5 leaflets that are rounded at the tip.

Sicklepod control with herbicides is difficult. An emergency use permit has recently been issued by the United States Environmental Protection Agency to allow the use of toxaphene for sicklepod control in soybeans grown in 5 southern states. Also, metribuzin can be applied postmergence directed, but this chemical is sometimes injurious to the soybeans.

Coffee senna (*Cassia occidentalis L.*) is similar in appearance to sicklepod, except that the seed pods are shorter, straighter, and more flattened. This species is widely distributed throughout the southeastern United States, and is an important weed within much of its geographic range.

Showy crotalaria (*Crotalaria spectabilis Roth.*) is widely distributed in the southeastern United States. This species is a problem weed because of the poisonous seeds that it produces. These seeds are very toxic to livestock, and a major source of poisoning is from the consumption of grain or feeds contaminated with crotalaria seeds. This species is also a member of the family Leguminosae.

*A. cassiae* is the first fungal pathogen that has been used to control these weeds.

SUMMARY OF THE INVENTION

The instant invention is a method which was developed to control sicklepod, coffee senna, and showy crotalaria, three important weeds in agricultural crops. The method consists of inoculating a field with the fungus *Alternaria cassiae*. This fungus controls all three weed species, but does not harm crop plants.

This invention differs from the prior art in that this fungus is a new pathogen of these weeds, and the processes of large scale production, formulation, and application are new. This foliar pathogen can be formulated and applied as a spray (wettable powder) or as granules that consist of the fungus and a carrier such as vermiculite, corn cob grits, or clay.

DESCRIPTION OF THE PREFERRED EMBODIMENTS

*Alternaria cassiae* Jurair and Khan is on deposit with USDA ARS Southern Weed Science Laboratory in Stoneville, Mississippi; with Mycological Services, Botony Department, University of Massachusetts, Amherst; and with the Agricultural Research Culture Collection (NRRL) in Peoria, Illinois, and have been assigned the following accession number: NRRL #12553. The address of the Agricultural Research Culture Collection (NRRL) is:

A. J. Lyons, Curator, ARS Patent Collection Culture Collection Research NRRC, 1815 N. University Street, Peoria, Illinois, 61604.

Spores (conidia) of this fungus are obclavate, muriform, smooth, light to dark-brown, and measure $92.0–332.0 \times 28.0–40\mu$ The *A. cassiae* used in these studies was isolated from diseased sicklepod seedlings grown in the greenhouse from seed that were field collected in the vicinity of Richton (Perry Co.) Mississippi, The fungus was isolated on potato dextrose agar, then subcultured on vegetable juice agar. The fungus sporulated profusely on V-8 juice agar in plastic petri dishes incubated at 25 C. with 12 hr diurnal light applied by two, 40-w cool-white fluorescent bulbs suspended 45 cm above the cultures.

*Alternaria cassiae*, NRRL #12553, was restricted in host range. Sicklepod, coffee senna, and crotalaria were the only plant species tested that were susceptible to the pathogen. The limited host range and highly virulent nature of *A. cassiae*, NRRL #12553, indicate that this pathogen has potential for use as a biological control agent for sicklepod, coffee senna, and showy crotalaria.

Preemergence or postemergence applications of granules can be used. The granular formulation of a foliar pathogen for soil application for preemergence weed control is difficult to recognize because soil-inhabiting organisms compete with the pathogen. The satisfactory performance of this fungus for preemergence weed control is determined by the method of formulation. All other prior art concerning weed control with plant pathogens have involved pathogens that controlled only one weed species. *Alternaria cassiae* controls multiple weed species without damage to crop plants. This use for this pathogen could not have been previously recognized or known because this fungus was not previously known to exist, and the pathogen had never been previously reported on the target weeds.

Spores of the *A. cassiae* are not produced in submerged liquid culture. These spores are produced in petri dishes, but this procedure is impractical for large scale production. This difficulty was overcome by a method for large scale production that represents new art.

EXAMPLE 1

Large scale production and granular formulation

Conidia from petri dish cultures were used to inoculate 10-L of liquid growth medium contained in 14-L vessels of a New Brunswick Model 214 fermeter. The liquid growth medium consisted of V-8 juice, 200 ml/L; calcium carbonate, 3 g/L; and sucrose 30 g/L in distilled water. Dow Corning Antifoam C was added to a final concentration of 0.02% (v/v). Conidia used in the greenhouse and field studies were produced from mycelia that were grown at 26 C. in submerged liquid culture with vigorous agitation and aeration. The mycelia were harvested 48 to 72 hr after inoculation, continued for 30 sec in a Waring Blender, then poured into 12 to 18 pans, (41 by 27 by 5.5 cm) and exposed to direct sunlight for 20 to 30 min. Sporulation was also induced by 10 min. exposures to light from sunlamps that were suspended 65 cm above the pans of mycelia. After the exposure to light the pans of mycelia were placed in unlighted chambers for 48 to 72 hr; then the spores and mycelia were air-dried at 35 C. The spores were harvested from surfaces of the mycelia with a cyclone collector dried over $CaCl_2$ for 48 hr, and stored in glass vials at 4 C. Spore concentrations were determined with a hemacytometer.

The fungus sporulated profusely in the laboratory studies, and 1.5 g of the spore preparation was commonly harvested from each pan of comminuted mycelia. The dried spore preparations contained about $9 \times 10^7$ spores/g as estimated with a hemacytometer. Spore germination was >90% on water agar incubated at 25 C. for 18 hr.

Granular preparations were produced from fermenter vessel cultures. After 48 to 72 h, the mycelia were harvested and comminuted. Blended mycleia from each 10-L culture were mixed with approximately 1000 g of horticultural vermiculite divided among 8 to 10 aluminum foil-lined plastic pans (41 by 27 by 5.5 cm). These pans of vermiculite and mycelia were exposed to 7 h diurnal light that was provided by two 40-w, cool-white florescent lamps. Recent studies have shown that the light requirement for sporulation can be provided by a single 20- to 30-min exposure to direct sunlight, or to light from sunlamps, as described previously. After 24 h, the surfaces of the vermiculite particles were covered with spores. The formulation of vermiculite-mycelia-spores was air-dried in an incubator at 35 C. for 24 to 48 h, then sieved, packaged in plastic bags, and stored at 4 C. Spore counts were estimated with a hemacytomer after spores were eluted from a known weight of the granular preparation into water. These granular preparations contained $1 \times 10^5$ conidia/g of the air-dried vermiculite preparation. These granular preparations are suitable for either preemergence or postemergence application.

TABLE 1

Reaction of various plant species to *Alternaria cassiae* isolated from sicklepod[a].

| Plant name | Disease reaction[b] |
|---|---|
| Caryophyllaceae | |
| Carnation (*Dianthus chinensis* L.) 'Dwarf Baby Mixed' | R+ |
| Compositae | |
| Chrysanthemum [*Chrysanthemum morifolium* (Ramat.) Hemsl.] 'Korean' | R+ |
| Cocklebur (*Xanthium pensylvanicum* Wallr.) | R+ |
| Dandelion (*Taraxacum officinale* Weber) | R+ |
| Sunflower (*Helianthus annuus* L.) 'Sungold' | R+ |
| Zinnia (*Zinnia elegans* Jacq.) 'B's Best' | R+ |
| Cucurbitaceae | |
| Cantaloupe (*Cucumis melo* L.) 'Harley's Best Jumbo' | R |
| Pumpkin (*Cucurbita pepo* L.) 'Jack-O'Lantern' | R+ |
| Squash [*Cucurbita pepo* var. *melopepo* (L.) Alef.] 'Golden Summer Crookneck' | R+ |
| Watermelon (*Citrullus vulgaris* Schrad.) 'Charleston Grey' | R |
| Leguminosae | |
| Alfalfa (*Medicago sativa* L.) 'Delta' | R+ |
| Bean, Lima (*Phaseolus limensis* Macf.) 'Burpee's Fordhook' | R+ |
| Bean, Pole (*Phaseolus vulgaris* L.) 'Romano' | R+ |
| Coffee senna (*Cassia occidentalis* L.) | S |
| Cowpea [*Vigna sinensis* (Torner) Savi] 'Early Ramshorn' | R+ |
| Hemp sesbania [*Sesbania exaltata* (Raf.) Cory] | R+ |
| Peanut (*Arachis hypogaea* L.) 'Tennessee Reds' | R+ |
| Showy crotalaria (*Crotalaria spectabilis* Roth) | S |
| Sicklepod (*Cassia obtusifolia* L.) | S |
| Soybean [*Glycine max* (L.) Merr.] | |
| 'Bragg' | R |
| 'Tracey' | R+ |
| 'Forrest' | R |
| Liliaceae | |
| Onion (*Allium cepa* L.) 'Yellow Globe' | R+ |
| Malvaceae | |
| Cotton (*Gossypium hirsutum* L.) 'Stoneville 213' | R+ |
| Okra [*Abelmoschus esculentus* (L.) Moench] 'Clemson Spineless' | R+ |
| Prickly sida (*Sida spinosa* L.) | R+ |
| Spurred anoda [*Anoda cristata* (L.) Schlecht.] | R+ |
| Velvetleaf (*Abutilon theophrasti* Medic.) | R+ |
| Solananceae | |
| Pepper (*Capsicum frutescens* L.) 'Large Cherry' | R |
| Tomato (*Lycopersicon esculentum* Mill.) | |
| 'Heinz 1439' | R |
| 'Rutger' | R |
| Convolvulaceae | |
| Morningglories (*Ipomoea* spp.) | R+ |
| Gramineae | |
| Corn (*Zea mays* L.) 'Truckers Favorite' | R+ |
| Oats (*Avena sativa* L.) | R |
| Sorghum [*Sorghum bicolor* (L.) Moench] 'Texas C 424' | R+ |
| Wheat (*Triticum aestivum* L.) 'Coker 68-15' | R |

[a]Twelve plants of each variety were sprayed with inoculum containing $1 \times 10^5$ spores/ml and surfactant. Controls were sprayed with surfactant and water only. Plants were evaluated daily for 14 days.
[b]Disease reaction: R = resistant; S = susceptible; + = phytotoxic injury.

EXAMPLE 2

Greenhouse studies

The plant species included in the greenhouse studies are listed in Table 1. Plants were grown in a commercial potting mix in peat strips that contained 12 plants each, and were fertilized weekly with a water soluble fertilizer. Temperatures ranged from 28 to 32 C. with 40 to 60% relative humidity. The day length was approximately 12 hr with 1650 $\mu$E.m$^{-2}$.s$^{-1}$ photosynthetically active radiation, as measured at noonday with Lambda PAR meter.

Plants in the cotyledon to first leaf stage of growth were sprayed to run-off with inoculum applied with an atomizer. Inoculation mixtures contained 0.02% (v/v) surfactant, nonoxynol (9 to 10 POE) [a(p-nonylphenyl)-w-hydroxypoly)oxyethylene)] in distilled water and 1×10$^5$ spores/ml. Control plants were sprayed with water and 0.02% surfactant only. All plants were placed in dew chambers for 8-10 hr at 20 C. The plants were then moved to greenhouse benches and evaluated daily for 14 days. All tests were repeated on at least two dates, and 12 plants were used for each treatment in each test.

The fungus was pathogenic and highly virulent to sicklepod seedlings. Most seedlings in the cotyledon to first leaf stage of growth were killed two to seven days after inoculation. The pathogen produced dark brown lesions 1-5 mm in diam on the leaves and stems within 2 days. The lesions enlarged with time on any remaining plants and produced severe stem cankers and defoliation within seven days. Coffee senna and showy crotalaria appeared to be as susceptible as sicklepod to the pathogen. Thirty other representative crop and weed species in nine families were resistant to the pathogen; however, phytotoxic damage was occasionally observed on inoculated leaves of several species (Table 1). Phytotoxic symptoms ranged from flecking to a marginal or interveinal 'burn' of inoculated leaves. These symptoms appeared within 48 to 72 hours after inoculation and did not increase in number or severity with time. Succulent tissues were most susceptible to damage. Greenhouse-grown soybeans occasionally exhibited phytotoxic symptoms, whereas these symptoms were greatly reduced or absent on field-grown soybeans. The phytotoxicity is attributed to the high concentrations of conidia contained in the inoculation mixtures. Phytotoxic injury was not observed in every test and this injury was never observed on the control plants. In other greenhouse studies the inoculum concentrations were reduced from 1×10$^5$ spores/ml to 2.5×10$^4$ spores/ml, and there was a decrease in phytotoxic injury, even though sicklepod seedlings exhibited severe disease symptoms.

TABLE 2

Effect of a foliar application of *Alternaria cassiae* to sicklepod in the field.[a]

| Treatment | Plants diseased | Plants severely stunted | Plants dead |
|---|---|---|---|
| Inoculated[b] | 100 | 48[c] | 32[c] |
| Control[d] | <1 | 0 | 0 |

[a]Plants from a 1 m$^2$ area within each plot were evaluated. Each value represents the average of three replications, 8 days after treatment. Each plot contained an average of 65 sicklepod plants/m$^2$.
[b]Plants were sprayed to wetness with a mixture of 2.5 × 10$^5$ spores/ml, surfactant, and water.
[c]Treatment significantly different at 1% level as determined by the t test.
[d]Plants were sprayed to wetness with surfactant and water only.

EXAMPLE 3

Field Studies

Randomized field plots 2.8 m square were replicated three times and planted with 100 soybean [*Glycine max* (L.) Merr. 'Forrest'] seeds and approximately 800 sicklepod seeds. The soybean seeds were planted to two rows/plot and the sicklepod seeds were broadcast. The plots were watered to field capacity by sprinkler irrigation to promote seed germination. Soybean and sicklepod plants in the cotyledon to first leaf stage of growth were sprayed to wetness with a suspension consisting of 0.1% surfactant and 2.5×10$^5$ spores/ml in distilled water that was applied with a garden sprayer. Control plots were sprayed with distilled water and 0.1% surfactant only. At 7 to 15 hr and 31 to 39 hr after inoculation, an overhead sprinkler sprayed water on the test area for 3 min/hr from 2200 hr to 0600 hr. Thus at least 8 hr of free moisture was present on the plants to stimulate spore germination and subsequent infection. Eight days after treatment, plants within a randomly selected 1 m$^2$ area in each plot were evaluated for disease symptoms. The t test was used to indicate differences between means.

The field plots contained an average of 65 sicklepod seedlings per m2. All sicklepod plants in the treated plots exhibited disease symptoms (Table 2). The number of sicklepod plants was reduced 32% and the number of sicklepod plants considered to be potentially competitive with the soybeans was reduced 80%. Injury was not observed on soybeans.

I claim:

1. A method for controlling multiple plant weeds of sicklepod, showy crotalaria, and coffee senna, comprising inoculating an agricultural field with an effective amount of fungus *Alternaria cassiae* to produce typical lesions in and kill said multiple weeds.

2. The method of claim 1 wherein the fungus is *Alternaria cassiae*, NRRL #12553.

3. The method of claim 1 wherein the fungus *Alternaria cassiae* is applied to the agricultural field as a spray or wettable powder.

4. The method of claim 1 wherein the fungus *Alternaria cassiae* is applied to the agricultural field as a granule that consists of the fungus and an inert carrier.

* * * * *